(12) United States Patent
Liu et al.

(10) Patent No.: US 12,044,653 B2
(45) Date of Patent: Jul. 23, 2024

(54) METHOD, APPARATUS AND SYSTEM FOR COMPENSATING BASELINE DRIFT IN GAS SENSOR

(71) Applicant: HONEYWELL INTERNATIONAL INC., Morris Plains, NJ (US)

(72) Inventors: Ling Liu, Morris Plains, NJ (US); Feng Liang, Morris Plains, NJ (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 433 days.

(21) Appl. No.: 16/884,592

(22) Filed: May 27, 2020

(65) Prior Publication Data

US 2020/0378921 A1  Dec. 3, 2020

(30) Foreign Application Priority Data

May 31, 2019 (CN) .......................... 201910469085.0

(51) Int. Cl.
*G01N 27/416* (2006.01)
*G01N 33/00* (2006.01)

(52) U.S. Cl.
CPC ..... *G01N 27/4163* (2013.01); *G01N 33/0047* (2013.01)

(58) Field of Classification Search
CPC .............. G01N 27/002; G01N 27/407; G01N 27/4115; G01N 27/4163; G01N 27/4175; G01N 33/0006

See application file for complete search history.

(56) References Cited

U.S. PATENT DOCUMENTS

| 4,303,613 A * | 12/1981 | Yasuda ................. G01N 27/16 324/71.5 |
| 4,475,378 A | 10/1984 | Boutonnat et al. |
| 4,498,330 A | 2/1985 | Hosoya |
| 5,055,269 A | 10/1991 | Palumbo et al. |
| 6,119,507 A | 9/2000 | Flosbach et al. |
| 2008/0028848 A1 | 2/2008 | Christensen |

(Continued)

FOREIGN PATENT DOCUMENTS

| CN | 101121050 A | 2/2008 |
| CN | 101482531 A | 7/2009 |

(Continued)

OTHER PUBLICATIONS

GB Combined Search and Examination Report Mailed on Nov. 12, 2020 for GB Application No. 2008111.

(Continued)

*Primary Examiner* — Matthew D Krcha
*Assistant Examiner* — Austin Q Le
(74) *Attorney, Agent, or Firm* — Alston & Bird LLP

(57) ABSTRACT

Methods, apparatuses, and systems for calculating a compensated reading of a gas sensing apparatus are provided. An example method includes causing a first supply of a working voltage to a sensing circuitry of the gas sensing apparatus, determining a first output of the sensing circuitry, causing a second supply of a stimulate voltage to the sensing circuitry, determining a second output of the sensing circuitry, and calculating a compensated reading of the gas sensing apparatus based at least in part on the first output and the second output.

6 Claims, 6 Drawing Sheets

(56) References Cited

U.S. PATENT DOCUMENTS

| | | | | |
|---|---|---|---|---|
| 2012/0192623 A1* | 8/2012 | Adami | ............... | G01N 33/0031 |
| | | | | 73/31.05 |
| 2015/0331016 A1 | 11/2015 | Malhan et al. | | |
| 2019/0086351 A1* | 3/2019 | Yamashita | ........... | G01N 33/005 |

FOREIGN PATENT DOCUMENTS

| | | | |
|---|---|---|---|
| CN | 105115532 | A | 12/2015 |
| CN | 105353092 | A | 2/2016 |
| IN | 367/MUM/2012 | | 3/2012 |
| JP | S59-180350 | A | 10/1984 |
| JP | 2005-029655 | A | 2/2005 |
| JP | 2007-010594 | A | 1/2007 |
| JP | 2011-058963 | A | 3/2011 |

OTHER PUBLICATIONS

GB Intent to Grant Mailed on Jun. 16, 2021 for GB Application No. 2008111, 2 pages.
CN Office Action, including Search Report Mailed on Jan. 22, 2024 for CN Application No. 201910469085, 9 page(s).
English Translation of CN Office Action dated Jan. 22, 2024 for CN Application No. 201910469085, 6 page(s).

\* cited by examiner

METHOD, APPARATUS AND SYSTEM FOR COMPENSATING BASELINE DRIFT IN GAS SENSOR

FIELD OF THE INVENTION

The present disclosure relates generally to methods, apparatuses, and systems for improving the accuracies of gas sensor readings, and more particularly, to methods, apparatuses, and systems for calculating a compensated reading that accounts for baseline drift in a low explosive limit gas sensor.

BACKGROUND

A gas sensor is a device that may detect the presence and/or concentration level of gaseous substance, including, for example, combustible gas, flammable gas, and/or toxic gas. For example, a low explosive limit (LEL) gas sensor may measure the concentration level of combustible and/or flammable gaseous substance (such as, for example, propane, and methane) up to one-hundred-percent (100%) of the low explosive limit of the gaseous substance. The term "lower explosive limit" refers to the minimum concentration level of gaseous substance in the air to support combustion when there is a source of ignition.

Many factors may affect the accuracies of LEL gas sensor readings, including, for example, mechanical shock and wear and tear of components through use. For example, a sudden force may be applied to a LEL gas sensor (e.g. when the LEL gas sensor is dropped to the ground), and the sudden force may affect the properties of various components within the LEL sensor. As another example, after being exposed under high temperature for a long period of time, the properties of various components within the LEL sensor may change, causing inaccuracies in the readings.

BRIEF SUMMARY

Various embodiments described herein relate to methods, apparatuses, and systems for improving the accuracies of gas sensor readings. In particular, various embodiments are related to calculating a compensated reading of a gas sensing apparatus.

In accordance with various examples of the present disclosure, a method calculating a compensated reading of a gas sensing apparatus is provided. The gas sensing apparatus may comprise a sensing circuitry, and the sensing circuitry may comprise a first circuit branch and a second circuit branch electronically coupled in parallel.

In some examples, the method may comprise causing a first supply of a working voltage to the sensing circuitry, determining a first output of the sensing circuitry, causing a second supply of a stimulate voltage to the sensing circuitry, determining a second output of the sensing circuitry, and calculating a compensated reading of the gas sensing apparatus based at least in part on the first output and the second output. The first output may correspond to a first voltage difference between the first circuit branch and the second circuit branch in response to the working voltage, and the second output may correspond to a second voltage difference between the first circuit branch and the second circuit branch in response to the stimulate voltage. The stimulate voltage may be lower than the working voltage. The compensated reading may correspond to a concentration level of a gaseous substance in contact with the gas sensing apparatus.

In some examples, a detector element and a compensator element may be electronically coupled on the first circuit branch, and a first resistor and a second resistor may be electronically coupled on the second circuit branch.

In some examples, the detector element comprises a first metal wire coil covered in a catalytic material, and the compensator element comprises a second metal wire coil covered in a non-catalytic material.

In some examples, the working voltage causes the gaseous substance to react on the detector element, and the stimulate voltage causes the gaseous substance to remain inert on the detector element.

In some examples, prior to causing the second supply of the stimulate voltage, the method further comprises: calculating a first reading of the gas sensing apparatus based at least in part on the first output, and determining that the first reading does not satisfy a threshold.

In some examples, the working voltage is between 2 volts (inclusive) and 4.5 volts (inclusive), and the stimulate voltage is between 0.1 volts (inclusive) and 0.2 volts (inclusive). In some examples, the working voltage is 3 volts, and the stimulate voltage is 0.2 volts.

In accordance with various examples of the present disclosure, a system for calculating a compensated reading is provided. The system may comprise a sensing circuitry, a processing circuitry in electronic communication with the sensing circuitry, and a memory circuitry in electronic communication with the processing circuitry. The sensing circuitry may comprise a first circuit branch and a second circuit branch electronically coupled in parallel. The memory circuitry may store computer program instruction. The computer program instruction may be configured to, with the processing circuitry, cause the system to cause a first supply of a working voltage to the sensing circuitry, determine a first output of the sensing circuitry, cause a second supply of a stimulate voltage to the sensing circuitry, determine a second output of the sensing circuitry, and calculate a compensated reading of the gas sensing apparatus based at least in part on the first output and the second output. In some examples, the first output corresponds to a first voltage difference between the first circuit branch and the second circuit branch in response to the working voltage. In some examples, the second output corresponds to a second voltage difference between the first circuit branch and the second circuit branch in response to the stimulate voltage. In some examples, the stimulate voltage is lower than the working voltage. In some examples, the compensated reading corresponds to a concentration level of a gaseous substance in contact with the sensing circuitry.

In accordance with various examples of the present disclosure, a computer program product is provided. The computer program product may comprise at least one non-transitory computer-readable storage medium having computer-readable program code portions stored therein. The computer-readable program code portions comprising an executable portion configured to: cause a first supply of a working voltage to a sensing circuitry of a gas sensing apparatus, determine a first output of the sensing circuitry, cause a second supply of a stimulate voltage to the sensing circuitry, determine a second output of the sensing circuitry, and calculate a compensated reading of the gas sensing apparatus based at least in part on the first output and the second output. The sensing circuitry may comprise a first circuit branch and a second circuit branch electronically coupled in parallel. The first output may correspond to a first voltage difference between the first circuit branch and the second circuit branch in response to the working voltage.

The second output may correspond to a second voltage difference between the first circuit branch and the second circuit branch in response to the stimulate voltage. The stimulate voltage may be lower than the working voltage. The compensated reading may correspond to a concentration level of a gaseous substance in contact with the gas sensing apparatus.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such component or feature may be optionally included in some embodiments, or it may be excluded.

As described above, many factors may affect the accuracies of gas sensor readings, which may result in "baseline drift." The term "baseline drift" refers to an erroneous positive or negative reading from a LEL gas sensor (which may suggest the presence of a combustible gaseous substance) when there is no combustible gaseous substance present. In this regard, various embodiments of the present disclosure may overcome the technical challenges associated with compensating for the baseline drift, and may improve the accuracies in sensor readings by, for example, calculating a compensated reading, details of which are described hereinafter.

Figure 1:
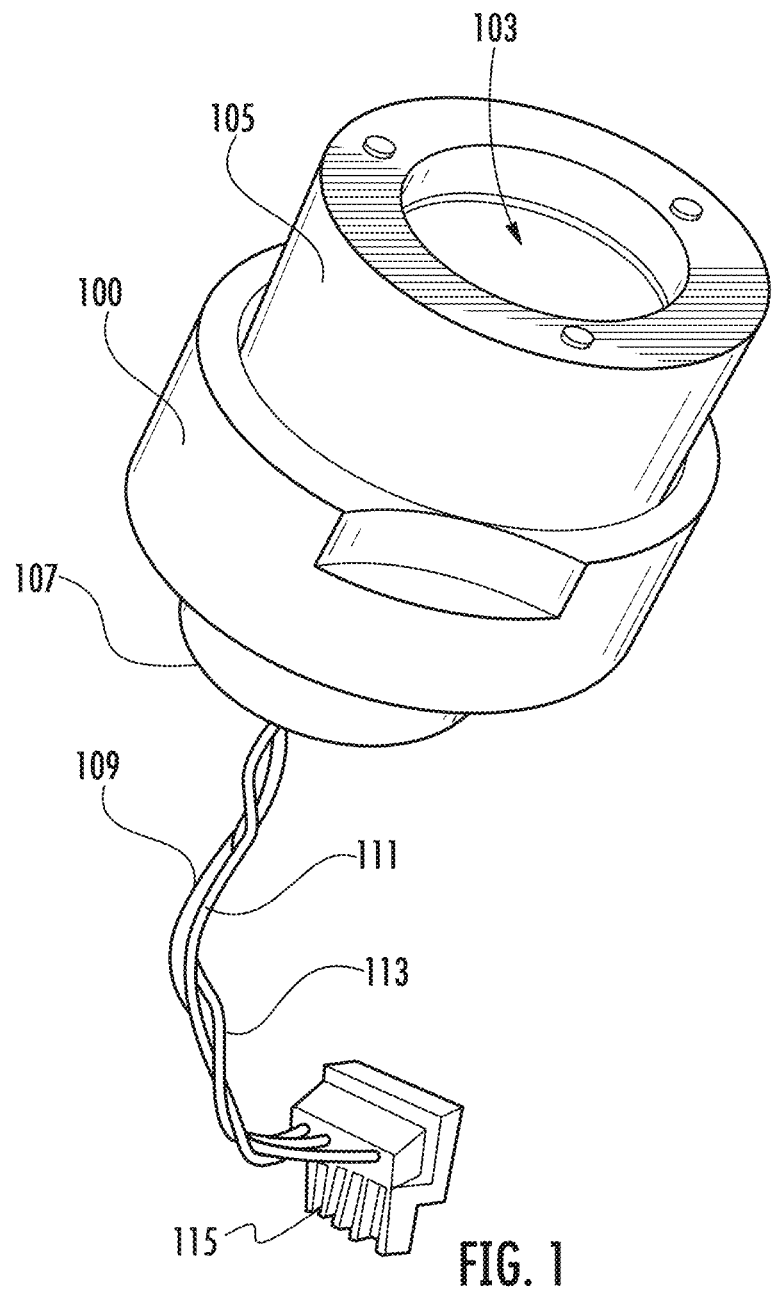
FIG. 1 illustrates an example perspective view of an example gas sensing apparatus in accordance with various embodiments of the present disclosure.

Referring now to FIG. 1, an example gas sensing apparatus 100 in accordance with various embodiments of the present disclosure is shown. In particular, the example gas sensing apparatus 100 may be a low explosive limit (LEL) sensor that is configured to detect and measure the concentration level of combustible gaseous substance.

The example gas sensing apparatus 100 as shown in FIG. 1 may comprise a cover member 103, a housing member 105, a mounting member 107, and one or more connection wires 109, 111, and 113.

The cover member 103 may be made of a material that has flame-proof properties and comprise porous structures, such as, for example, sintered stainless steel or sintered metallic fibers. The cover member 103 may be in contact with the gaseous substance that the example gas sensing apparatus 100 is configured to detect and/or measure. The porous structures of the cover member 103 may allow the gaseous substance to pass through the cover member 103 and enter into the example gas sensing apparatus 100. The flame-proof properties of the cover member 103 may prevent any combustion and/or flame that occurred within the example gas sensing apparatus 100 from spreading outside the gas sensing apparatus 100.

The housing member 105 of the example gas sensing apparatus 100 may be made of a metal alloy, such as stainless steel or carbon steel. In some examples, the housing member 105 may be in a shape similar to a hollow cylinder shape. In some examples, the housing member 105 may be in other shapes, such as but not limited to a hollow hexagonal prism shape, a hollow cube shape, without deviating from the scope of the present disclosure.

The housing member 105, together with the cover member 103, may form an enclosure that houses various components of the example gas sensing apparatus 100, such as, but is not limited to, a header plate. The header plate may comprise two or more bead members that are disposed on the surface of the header plate and in contact with the gaseous substance that passed through the cover member 103. Each of the bead members may comprise a metal wire coil, which may be coated with material to form a bead shape. Example details of an example header plate is illustrated and described in connection with FIG. 3 below.

Example details of an example bead member is illustrated and described in connection with FIG. 5 below.

The mounting member 107 of the example gas sensing apparatus 100 may be attached to the housing member 105, and may provide a mechanical interface between the example gas sensing apparatus 100 and other apparatus(es) that the example gas sensing apparatus 100 may be connected to. For example, the mounting member 107 may be installed in a collecting cone to facilitate the detection and measurement of combustible gaseous substance by the example gas sensing apparatus 100. In some examples, the mounting member 107 may be in a shape similar to a hollow cylinder shape. In some examples, the mounting member 107 may be in other shapes, such as but not limited to a hollow hexagonal prism shape, a hollow cube shape, without deviating from the scope of the present disclosure.

In some examples, the example gas sensing apparatus 100 may comprise one or more connection wires 109, 111, and 113. The connection wires 109, 111, and 113 may be connected to electronic element(s) within the example gas sensing apparatus 100 (such as, for example, metal wire coils of the bead members disposed on header plate), and may transmit electronic signals associated with these electronic element(s) to one or more other circuitries, such as the signal adapter 115.

In some examples, the signal adapter 115 may be installed on a printed circuit board, such as electronic signals transmitted by the connection wires may be analyzed by a processing circuitry, details of which are described in connection with FIGS. 6-8 below.

While FIG. 1 illustrates the example gas sensing apparatus 100 as having three connection wires, in some examples, an example gas sensing apparatus may have less than three or more than three connection wires, without deviating from the scope of the present disclosure.

Additionally or alternatively, the example gas sensing apparatus 100 may comprise one or more metal pins that are connected to electronic element(s) within the example gas sensing apparatus 100 (such as, for example, metal wire coils of the bead members disposed on the header plate), and may transmit electronic signals associated with these electronic element(s) to one or more other circuitries.

Figure 2:
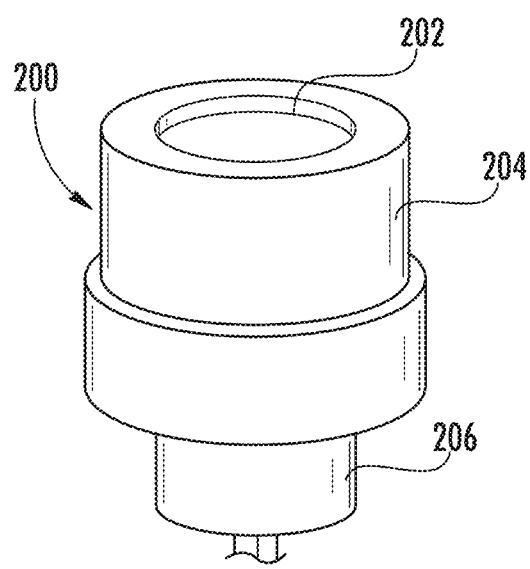
FIG. 2 illustrates an example perspective view of various components of an example gas sensing apparatus in accordance with various embodiments of the present disclosure.
Figure 3:
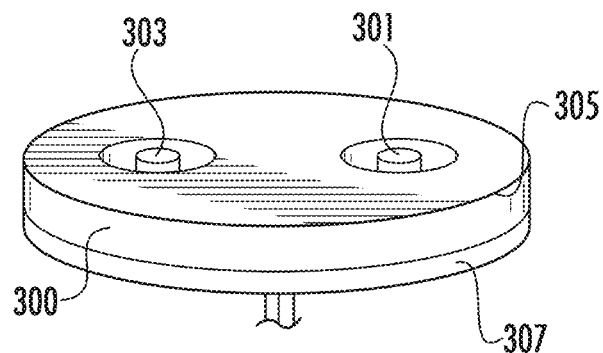
FIG. 3 illustrates an example perspective view of various components of an example gas sensing apparatus in accordance with various embodiments of the present disclosure.

Referring now to FIG. 2 and FIG. 3, various example components of an example gas sensing apparatus is shown. In particular, FIG. 2 illustrates an example outer shell 200 of an example gas sensing apparatus, and FIG. 3 illustrates an example header plate 300 of an example gas sensing apparatus.

The example outer shell 200 as shown in FIG. 2 may comprise a cover member 202, a housing member 204, and a mounting member 206. In some examples, the cover member 202 may be similar to the cover member 103 described above in connection with FIG. 1. In some examples, the housing member 204 may be similar to the housing member 105 described above in connection with FIG. 1. In some examples, the mounting member 206 may be similar to the mounting member 107 described above in connection with FIG. 1.

Referring now to FIG. 3, an example header plate 300 is shown. The header plate 300 may comprise a pair of bead members 301 and 303, a mounting disc 305 and a printed circuit board 307.

As described above in connection with FIG. 1, the bead members 301 and 303 may be disposed on the surface of the header plate 300 and in contact with the gaseous substance that passed through a cover member of an example gas sensing apparatus (for example, the cover member 103 of the example gas sensing apparatus 100 as described above in connection with FIG. 1). Each of the bead members 301 and 303 may comprise a metal wire coil, such as a platinum wire coil. When voltage is supplied to the metal wire coil, the metal wire coil may generate heat, resulting in temperature increase of the bead member.

In some examples, each of the bead members 301 and 303 may comprise material(s) that covers the metal wire coil and form a bead shape. In particular, one of the bead members (for example, bead member 301) may comprise a porous alumina material and/or other catalytic material that covers the metal wire coil (such bead member may also be referred to as a "detector element" hereinafter). In contrast, the other bead member (for example, bead member 303) may comprise non-catalytic material (such bead member may also be referred to as a "compensator element" hereinafter).

In some example, the metal wire coil of the bead member 301 may have the same electrical resistance as the metal wire coil of the bead member 303. In some examples, the bead members 301 and 303 may be of the same shape. In some examples, the shape of the bead member 301 may be different from the shape of the bead member 303.

As shown in FIG. 3, the bead member 301 and the bead member 303 may be disposed on mounting disc 305 of the header plate 300. In particular, each of the bead member 301 and the bead member 303 may be disposed within a separate aperture on the surface of the mounting disc 305. In some examples, the mounting disc 305 may comprise material(s) that is resistant to high temperature, such as, for example, polytetrafluoroethylene (PTFE).

The printed circuit board 307 may be disposed beneath the mounting disc 305. The printed circuit board 307 may mechanically support and electrically connect various electronic components (such as, for example, various electronic components for a sensing circuitry). Further, the bead member 301 and the bead member 303 may be connected to various electronic components on the printed circuit board 307 (such as the sensing circuitry) through, for example, metal leads. Example metal leads are illustrated and described below in connection with FIG. 4. An example sensing circuitry is illustrated and described below in connection with FIG. 6.

Figure 4:
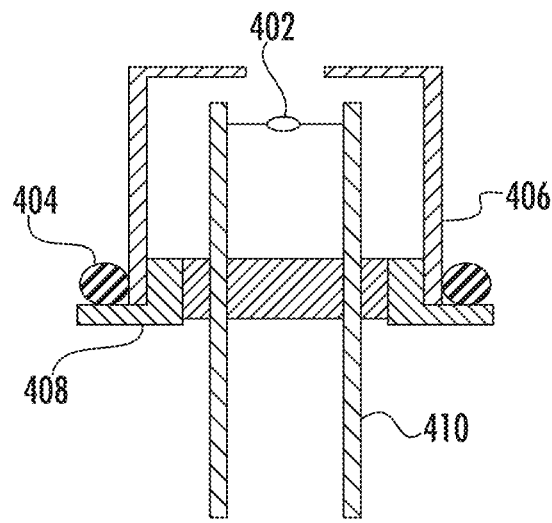
FIG. 4 illustrates an example diagram of various components of an example gas sensing apparatus in accordance with various embodiments of the present disclosure.
Figure 5:
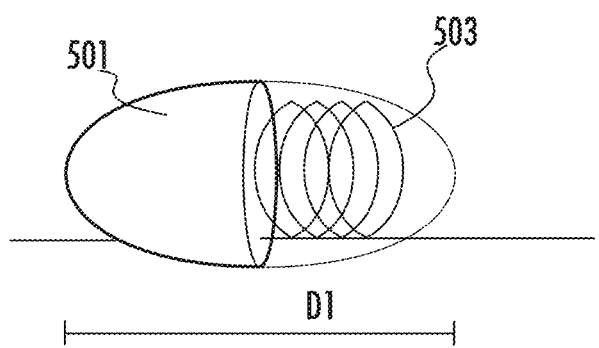
FIG. 5 illustrates an example diagram of various components of an example gas sensing apparatus in accordance with various embodiments of the present disclosure.

Referring now to FIG. 4 and FIG. 5, example diagrams illustrating various example structures associated with an example bead member are provided.

In the embodiment as shown in FIG. 4, the bead member 402 may be connected to a pair of metal leads 410. In particular, the metal leads 410 may be connected to the metal wire coil within the bead member 402, and the metal leads 410 may comprise material such as platinum.

Figure 6:
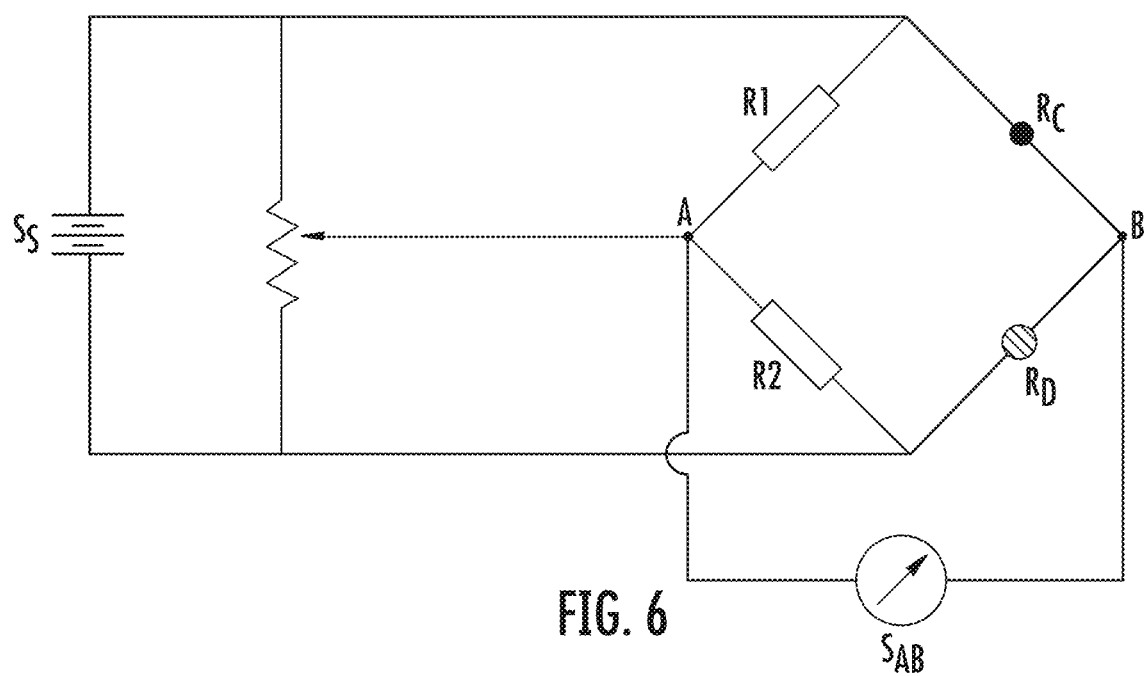
FIG. 6 illustrates an example circuit diagram of an example sensing circuitry in accordance with various embodiments of the present disclosure.

In some examples, the ends of the metal leads 410 may be connected to various electronic components, such as, for example, a sensing circuitry as shown in FIG. 6. In other words, the bead member 402 may be connected to the sensing circuitry through the metal leads 410.

Further, the bead member 402 may be housed within a container member 406. The container member 406 may be made of metal, and may further comprise an aperture that allows the bead member 402 to be in contact with the to-be-detected gaseous substance. In some examples, the container member 406 may be secured to a header plate 408 through a sealing ring 404. The sealing ring 404 may comprise elastic material, such as, for example, rubber and/or silicon.

Referring now to FIG. 5, an example internal structure of an example bead member is shown. In particular, FIG. 5 provides a half cross-sectional view that illustrates a metal wire coil 503 disposed within a cover member 501.

As described above, an example gas sensing apparatus may comprise two bead members. One of the bead member (the "detector element") may have cover member 501 that comprises catalytic material. The catalytic material may allow catalytic combustion or oxidation to occur. In this regard, when a voltage is supplied to the metal wire coil 503, the metal wire coil 503 may heat the bead member. When the voltage is high enough, the high temperature of the bead member may cause the combustible gaseous substance to react on the detector element (such as catalytic oxidation).

The other bead member (the "compensator element") may have cover member 501 that comprises non-catalytic material, and may resemble the detector element in other respects. In other words, the compensator element does not trigger catalytic combustion or oxidation, and the combustible gaseous substance may remain inert on the compensator element.

In some examples, the length D1 of the bead member is one millimeter (1 mm). In some examples, the length D1 may be of other suitable value, without deviating from the scope of the present disclosure.

Referring now to FIG. 6, an example circuit diagram illustrating an example sensing circuitry of an example gas sensing apparatus is shown.

As described above, the metal wire coil of bead members of the example gas sensing apparatus may be connected to the sensing circuitry. As shown in FIG. 6, the metal wire coil of the detector element (i.e. bead member with catalytic material) may have an electrical resistance of $R_D$, and the metal wire coil of the compensator element (i.e. bead member with non-catalytic material) may have an electrical resistance of $R_c$.

In the embodiment as shown in FIG. 6, the sensing circuitry may comprise a Wheatstone bridge circuit. In particular, the Wheatstone bridge circuit may comprise a first circuit branch and a second circuit branch that are electronically coupled in parallel. As shown in FIG. 6, the detector element and the compensator element may be connected on the first circuit branch of the Wheatstone bridge circuit, and a first resistor $R_1$ and a second resistor $R_2$ may be connected on the second circuit branch of the Wheatstone bridge circuit.

Further, a voltage ($S_S$) may be supplied to power the Wheatstone bridge circuit. In some examples, the value of the voltage ($S_S$) may be adjustable and/or controllable. For example, a processing circuitry may be in electronic communication with an adjustable power supply to cause the supplies of different voltages to power the Wheatstone bridge circuit. Example voltages may include, for example, a working voltage ($S_1$) and a stimulate voltage ($S_2$), details of which are described in connection with FIG. 7 and FIG. 8 below.

Referring back to FIG. 6, a voltage difference ($S_{AB}$) between the first circuit branch and the second circuit branch (i.e. between point A and point B of the Wheatstone bridge circuit) may be calculated based on the following equation:

$$S_{AB} = \left(\frac{R_2}{R_1 + R_2} - \frac{R_D}{R_D + R_C}\right) \times S_S$$

In some examples, the resistor $R_1$ and the resistor $R_2$ may have the same electrical resistance value. The detector element and the compensator element may each comprise a metal wire coil having the same electrical resistance. When the detector element and the compensator element are at the same temperature (e.g. when there is no catalytic combustion or oxidation), $R_C$ has the same value as $R_D$. In other words, when there is no combustible gaseous substance present:

$$R_C = R_D; S_{AB} \approx 0$$

When there is combustible gaseous substance present, the combustible gaseous substance may cause the catalytic oxidation of the detector element (but not the compensator element, as described above). The oxidation may further increase the temperature of the detector element, while the temperature of the compensator element is unaffected by the presence of combustible gaseous substance. The increased temperature of the detector element may cause the change in the electrical resistance of the detector element. As a result, the difference in temperatures between the detector element and the compensator element may be registered as the difference in the correspondence electrical resistances. In other words, when there is combustible gaseous substance present:

$$R_C \neq R_D; S_{AB} \neq 0$$

Further, the new electrical resistance of the detector element ($R_D'$) due to the temperature increase may be calculated based on the following equation:

$$R_D' = \frac{R_2 \times S_s - (R_1 + R_2) \times S_{AB}}{R_1 \times S_s - (R_1 + R_2) \times S_{AB}} \times R_c$$

In examples where the resistor $R_1$ and the resistor $R_2$ have the same electrical resistance value, the new electrical resistance of the detector element ($R_D'$) may be calculated based on the following equation:

$$R_D' = \frac{S_s - 2 \times S_{AB}}{S_s - 2 \times S_{AB}} \times R_c$$

As described above, when there is no combustible gaseous substance present, the voltage difference ($S_{AB}$) should be close to zero. However, many factors (such as mechanical shock and wear and tear of resistor components) may result in the voltage difference ($S_{AB}$) deviating from zero even when there is no combustible gaseous substance present, resulting in a "baseline drift."

In some examples, when baseline drift is observed, a calibration process may be performed to adjust the electrical resistance of the Wheatstone bridge circuit through, for example, adjusting the electrical resistance of a variable resistor in the Wheatstone bridge circuit (as shown in FIG. 6). For example, calibration gas (i.e. fresh air without any combustible gaseous substance) may be applied to the gas sensing apparatus, and the variable resistor may be adjusted so that the voltage difference ($S_{AB}$) is set to zero.

However, this calibration process may have some shortcomings. For example, when the gas sensing apparatus is immovably secured at a particular location (for example, in an environment with combustible gaseous substance), it may be challenging to provide calibration gas to the gas sensing apparatus to perform this calibration process. As another example, a user may erroneously apply a bottle of air mixed with combustible gaseous substance on the mistaken belief that there is no combustible gaseous substance in the bottle, which may result in further inaccuracies.

Various embodiments of the present disclosure provide example methods, systems and apparatuses that may overcome the above shortcomings. In some example embodiments, there may be no need for calibration gas when calculating a compensated reading of the gas detecting apparatus. As such, some example embodiments of the present disclosure may improve accuracies of gas sensor readings.

Figure 7:
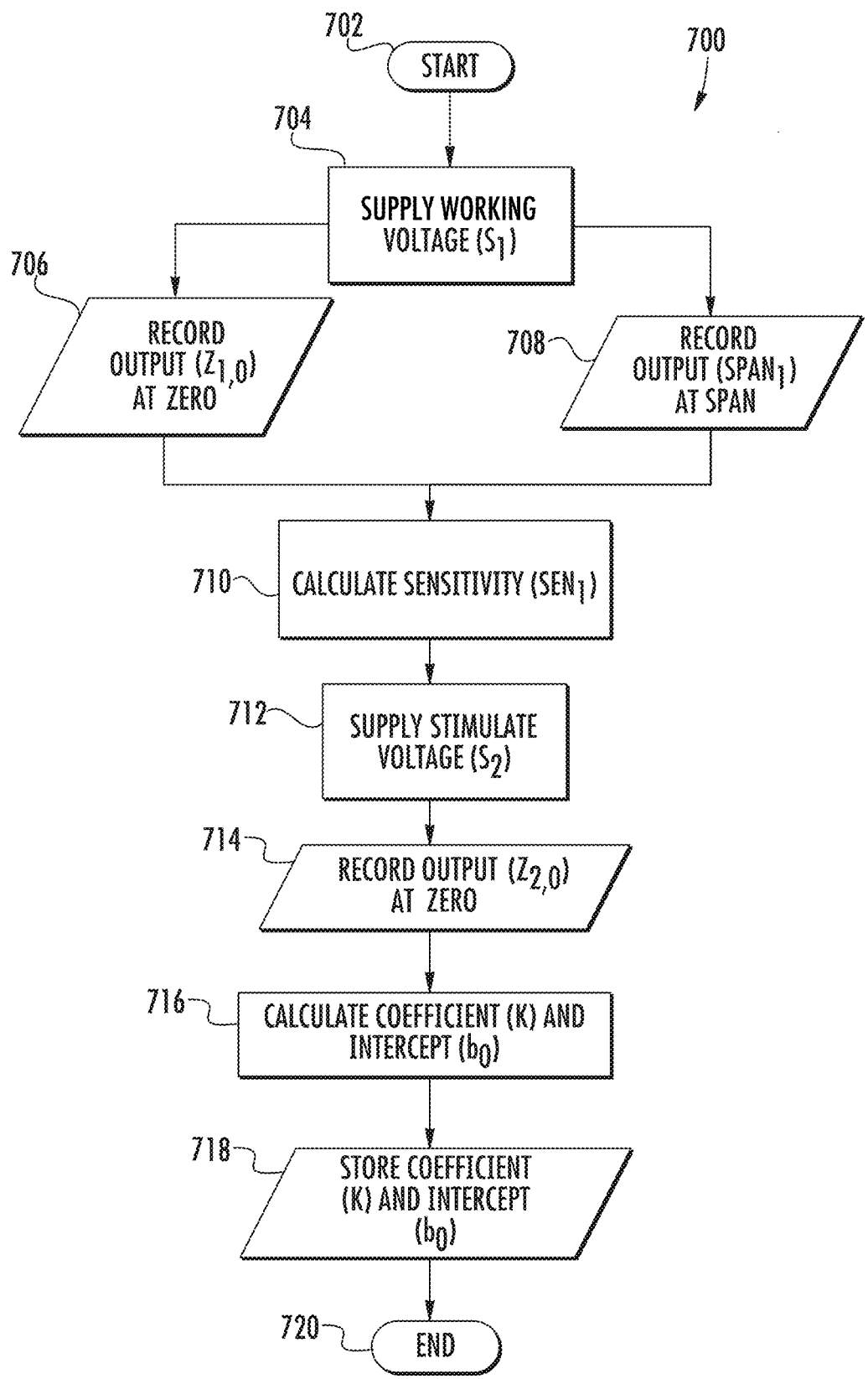
FIG. 7 illustrates an example flow chart in accordance with various embodiments of the present disclosure.
Figure 8:
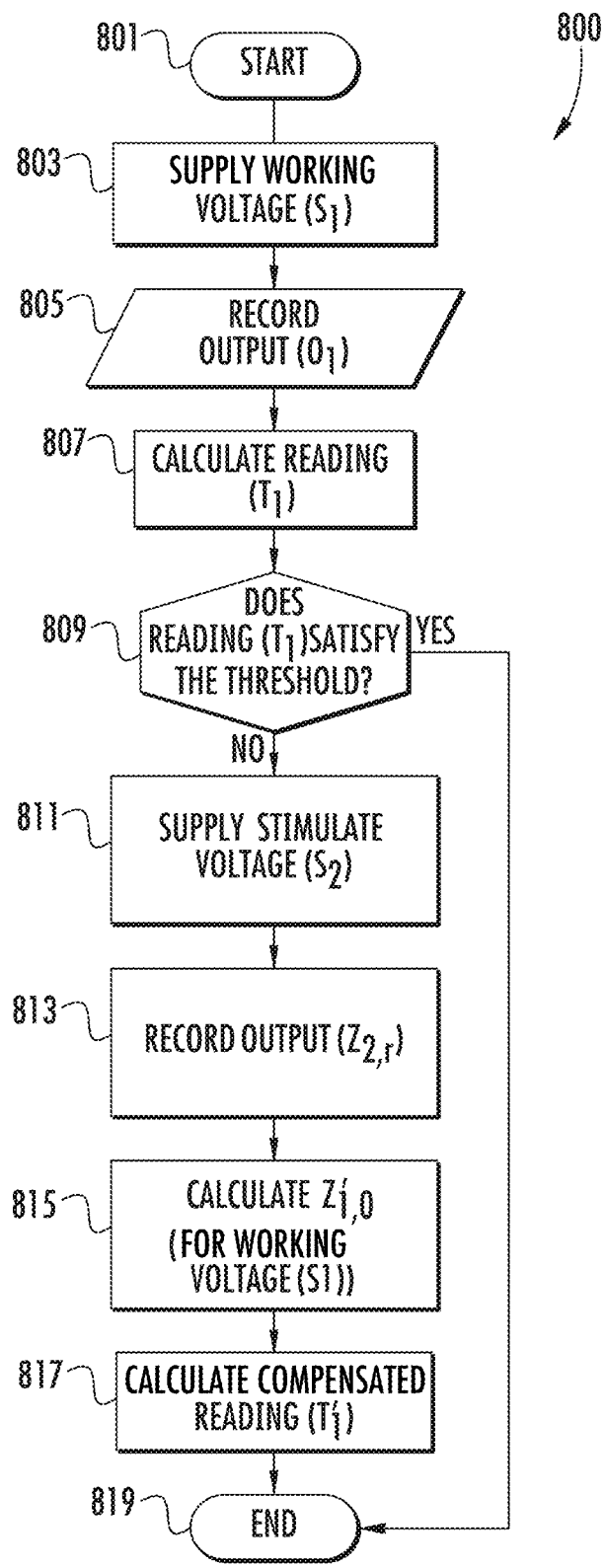
FIG. 8 illustrates an example flow chart in accordance with various embodiments of the present disclosure.

Referring now to FIG. 7 and FIG. 8, some of the example methods associated with calculating a compensated reading of a gas sensing apparatus in accordance with various embodiments are illustrated.

In some examples, each block of the flowchart, and combinations of blocks in the flowchart, may be implemented by various means such as hardware, firmware, circuitry and/or other devices associated with execution of software including one or more computer program instructions.

In some examples, one or more of the procedures described in figures may be embodied by computer program instructions, which may be stored by a memory circuitry (such as a non-transitory memory) of a system employing an embodiment of the present disclosure and executed by a processing circuitry (such as a processor) of the system. These computer program instructions may direct the system to function in a particular manner, such that the instructions stored in the memory circuitry produce an article of manufacture, the execution of which implements the function specified in the flowchart block(s). Further, the system may comprise one or more other circuitries, such as, for example, the sensing circuitry described above in connection with FIG. 6. Various circuitries of the system (such as the sensing circuitry, the processing circuitry, and the memory circuitry) may be in electronic communication between and/or among each other to transmit data to and/or receive data from each other.

In some examples, embodiments may take the form of a computer program product on a non-transitory computer-readable storage medium storing computer-readable program instructions (e.g. computer software). Any suitable computer-readable storage medium may be utilized including non-transitory hard disks, CD-ROMs, flash memory, optical storage devices, or magnetic storage devices.

In some examples, each block of the flowchart, and combinations of blocks in the flowchart, may be performed manually.

Referring now to FIG. 7, an example method 700 in accordance with some embodiments of the present disclosure is illustrated. In particular, the example method 700 illustrates example embodiments of calculating various parameters for calculating a compensated reading.

In some examples, the method 700 may be performed by a processing circuitry (for example, but not limited to, an application-specific integrated circuit (ASIC), a central processing unit (CPU)). In some examples, the processing circuitry may be electrically coupled to and/or in electronic communication with other circuitries of the example gas sensing apparatus, such as, but not limited to, a sensing circuitry (as shown in, for example, FIG. 6), a memory circuitry (such as, for example, random access memory (RAM) for storing computer program instructions), and/or a display circuitry (for rendering device readings on a display).

The method 700 starts at block 702. At block 704, the processing circuitry may cause the supply of a working voltage ($S_1$) to a sensing circuitry of an example gas sensing apparatus (such as the sensing circuitry described above in connection with FIG. 6). The working voltage ($S_1$) may be a default working voltage for the sensing circuitry. In some examples, the working voltage ($S_1$) may cause combustible gaseous substance to react on the detector element, as described above in connection with FIG. 6.

In some examples, the working voltage ($S_1$) may be a constant voltage between 2 V (inclusive) and 4.5 V (inclusive). In some examples, the working voltage ($S_1$) may be chosen from the following values: 2.3 V, 2.5 V, 2.8 V, 3 V, 3.5 V, and 4.25 V. In some examples:

$$S_1 = 3\ V$$

After the working voltage ($S_1$) is supplied to the sensing circuitry, the processing circuitry may record an output ($Z_{1,0}$) based on a constant, non-transitory signal received from the sensing circuitry under a "zero condition" at block 706, and may record an output ($SPAN_1$) based on a constant, non-transitory signal from the sensing circuitry under a "span condition" at block 708.

The term "zero condition" refers to a condition when no combustible gaseous substance is in contact with the gas sensing apparatus. In other words, under zero condition, there is no combustible gaseous substance (for example, fresh air without any combustible gaseous substance) in contact with the detector element of the sensing circuitry (as described above in connection with FIG. 6).

The term "span condition" refers to a condition when combustible gaseous substance having a known concentration level ($CON_1$) is in contact with the gas sensing apparatus. As a non-limiting example, the span condition may be methane gas at fifty percent (50%) of its lower explosive limit being in contact with the gas sensing apparatus. In other words, under the span condition, the detector element of the sensing circuitry (as described above in connection with FIG. 6) may be in contact with combustible gas having a known concentration level ($CON_1$), and the electrical resistance of the detector element may change as described above at least in connection with FIG. 6.

In some examples, each of the output ($Z_{1,0}$) and the output ($SPAN_1$) may correspond to the voltage difference in a Wheatstone bridge circuit of the sensing circuitry under the corresponding condition. For example, the processing circuitry may record an output ($Z_{1,0}$) that corresponds to the voltage difference ($S_{AB}$) of the Wheatstone bridge circuit as shown in FIG. 6 under the zero condition and in response to the working voltage ($S_1$), and may record an output ($SPAN_1$) that corresponds to the voltage difference ($S_{AB}$) of the Wheatstone bridge circuit as shown in FIG. 6 under the span condition and in response to the working voltage ($S_1$). Further, any change in the electrical resistance of the detector element may be calculated based at least in part on the voltage difference ($S_{AB}$) as described above at least in connection with FIG. 6.

In some examples, the processing circuitry may store the values of outputs ($Z_{1,0}$) and ($SPAN_1$) in a memory circuitry that is in electronic communication with the processing circuitry.

In some examples, block 706 may be performed prior to block 708. In other words, the processing circuitry may receive and record the output ($Z_{1,0}$) from the sensing circuitry under the zero condition prior to receiving and recording the output ($SPAN_1$) from the sensing circuitry under the span condition.

In some examples, block 706 may be performed after block 708. In other words, the processing circuitry may receive and record the output ($Z_{1,0}$) from the sensing circuitry under the zero condition after receiving and recording the output ($SPAN_1$) from the sensing circuitry under the span condition.

After recording the values of outputs ($Z_{1,0}$) and ($SPAN_1$), the processing circuitry may calculate sensitivity ($SEN_1$) of the gas sensing apparatus at block 710. The sensitivity ($SEN_1$) indicates how much the sensing circuitry output changes (for example, the voltage difference ($S_{AB}$) of the sensing circuitry) when the input quantity being measured changes (for example, the concentration level of combustible gaseous substance).

As described above, the combustible gaseous substance may be affected the electrical resistance of the detector element in the sensing circuitry, but not the electrical resistance of the compensator element in the sensing circuitry. The higher the concentration level of combustible gaseous substance, the higher the difference between the electrical resistances of the detector element and the compensator element, resulting in a higher voltage difference ($S_{AB}$) in the Wheatstone bridge circuit of the sensing circuitry.

In some examples, the sensitivity ($SEN_1$) can be calculated based at least in part on the outputs ($Z_{1,0}$) and ($SPAN_1$). In some example, the sensitivity ($SEN_1$) can be calculated based on the following equation:

$$SEN_1 = \frac{SPAN_1 - Z_{1,0}}{CON_1}$$

where $SPAN_1$ is the output under the span condition, $Z_{10}$ is output under the zero condition, and $CON_1$ is the concentration level of combustible gaseous substance at the span condition.

At block 712, the processing circuitry may cause the supply of a stimulate voltage ($S_2$) to a sensing circuitry of an example gas sensing apparatus (such as the sensing circuitry described above in connection with FIG. 6).

In some examples, the stimulate voltage ($S_2$) is lower than the working voltage ($S_1$). In some examples, the stimulate voltage ($S_2$) may not cause any combustible gaseous substance to react on the detector element. In other words, the stimulate voltage ($S_2$) may be low enough to avoid overheating the detector element (for example, the temperature being lower than 200° C.), and thus may cause the gaseous substance to remain inert on the detector element.

In some examples, the stimulate voltage ($S_2$) may be a constant voltage between 0.1 V (inclusive) and 0.2 V (inclusive). In some examples:

$S_2 = 0.2$ V

After the stimulate voltage ($S_2$) is supplied to the sensing circuitry, the processing circuitry may record the value of an output ($Z_{2,0}$) based on a constant, non-transitory signal received from the sensing circuitry at block 714.

In some examples, the value of output ($Z_{2,0}$) may correspond to a voltage difference in the Wheatstone bridge circuit. For example, referring back to FIG. 6, the value of output ($Z_{2,0}$) may correspond to the voltage difference ($S_{AB}$) of the Wheatstone bridge circuit as shown in FIG. 6 in response to the stimulate voltage ($S_2$). In some examples, the processing circuitry may store the recorded value of output ($Z_{2,0}$) in the memory circuitry that is in electronic communication with the processing circuitry.

As described above, in some examples, the stimulate voltage ($S_2$) may cause the gaseous substance to remain inert on the detector element. As a result, the value of output ($Z_{2,0}$) may only indicate the voltage difference (or the corresponding electrical resistance difference) between the detector element and the compensator element that is not caused by any combustible gaseous substance that may or may not be present.

At block 716, the processing circuitry may calculate the coefficient (K) and the intercept ($b_0$) of the sensing circuitry (such as the sensing circuitry as described above in connection with FIG. 6). The coefficient (K) and the intercept ($b_0$) may indicate the amount of baseline drift of the sensing circuitry due to, for example, mechanical shock and wear and tear of the detector element and the compensator element. In some examples, the coefficient (K) may be calculated based on the following equation:

$$k = \frac{Z_{1,0} - Z_{2,0}}{S_1 - S_2}$$

where $Z_{1,0}$ is the output under the zero condition when working voltage is supplied, $Z_{2,0}$ is the output when stimulate voltage is supplied, $S_1$ is the working voltage, and $S_2$ is the stimulate voltage.

In some examples, the intercept ($b_0$) may be calculated based on the following equation:

$$b_0 = \frac{Z_{1,0} \times (S_1 - S_2) - S_1 \times (Z_{1,0} - Z_{2,0})}{S_1 - S_2}$$

where $Z_{1,0}$ is output under the zero condition when working voltage is supplied, $Z_{20}$ is the output when stimulate voltage is supplied, $S_1$ is the working voltage, and $S_2$ is the stimulate voltage.

After calculating the coefficient (K) and the intercept ($b_0$), the processing circuitry may store the coefficient (K) and the intercept ($b_0$) in a memory circuitry that is in electronic communication with the processing circuitry at block 718. The coefficient (K) and the intercept ($b_0$) may be utilized to calculate a compensated reading of the gas sensing apparatus, examples of which are illustrated and described below in connection with FIG. 8.

The method 700 ends at block 720.

Referring now to FIG. 8, an example method 800 in accordance with some embodiments of the present disclosure is illustrated. In particular, the example method 800 illustrates example embodiments of calculating a compensated reading for a gas sensing apparatus.

In some examples, the method 800 may be performed by a processing circuitry (for example, but not limited to, an application-specific integrated circuit (ASIC), a central processing unit (CPU)). In some examples, the processing circuitry may be electrically coupled to and/or in electronic communication with other circuitries of the example gas sensing apparatus, such as, but not limited to, a sensing circuitry (as shown in, for example, FIG. 6), a memory circuitry (such as, for example, random access memory (RAM) for storing computer program instructions), and/or a display circuitry (for rendering device readings on a display).

The method 800 starts at block 801. At block 803, the processing circuitry may cause a first supply of a working voltage ($S_1$) to a sensing circuitry of an example gas sensing apparatus (such as the sensing circuitry described above in connection with FIG. 6). As described above, the working voltage ($S_1$) may be a default working voltage for the sensing circuitry, and may cause combustible gaseous substance to react on the detector element, as described above in connection with FIG. 6.

In some examples, the working voltage ($S_1$) may be a constant voltage between 2 V (inclusive) and 4.5 V (inclusive). In some examples, the working voltage ($S_1$) may be chosen from the following values: 2.3 V, 2.5 V, 2.8 V, 3 V, 3.5 V, and 4.25 V. In some examples:

$$S_1=3V$$

In some examples, the working voltage ($S_1$) of block 803 of FIG. 8 may be the same as the working voltage ($S_1$) of block 704 of FIG. 7.

After the working voltage ($S_1$) is supplied to the sensing circuitry, the processing circuitry may determine and record a first output ($O_1$) based on a constant, non-transitory signal received from the sensing circuitry at block 805.

In some examples, the first output ($O_1$) may correspond to a first voltage difference of the sensing circuitry in response to the working voltage ($S_1$). For example, referring back to FIG. 6, the sensing circuitry may comprise a Wheatstone bridge circuit, and the processing circuitry may determine and record the first output ($O_1$) that corresponds to the voltage difference ($S_{AB}$) in the Wheatstone bridge circuit of the sensing circuitry.

In some examples, when the working voltage ($S_1$) is supplied to the sensing circuitry, the sensing circuitry may be in contact with a combustible gaseous substance that the gas sensing apparatus is detecting. In such examples, the first voltage difference may be caused by, for example, baseline shift of the gas sensing apparatus (e.g. the change in electrical resistance of the detector element that is not due to detecting combustible gaseous substance) and reaction of the combustible gaseous substance on the detector element.

At block 807, the processing circuitry may calculate a first reading ($T_1$) of the gas sensing apparatus. The first reading ($T_1$) of the gas sensing apparatus may correspond to a concentration level of the combustible gaseous substance as determined by the gas sensing apparatus, and may be calculated based at least in part on the first output ($O_1$). In some examples, the first reading ($T_1$) may be calculated based on the following equation:

$$T_1 = \frac{O_1 - Z_{1,0}}{SEN_1}$$

where $O_1$ is the first output from the sensing circuitry in response to the simulate voltage $S_1$, $Z_{1,0}$ is the output recorded under the zero condition and when the simulate voltage $S_1$ is supplied (for example, as described in connection with block 706 of FIG. 7), and $SEN_1$ is the sensitivity of the sensing circuitry (for example, as described in connection with block 710 of FIG. 7).

At block 809, the processing circuitry may determine whether the first reading ($T_1$) satisfies a threshold. For example, the circuitry may determine whether the first reading ($T_1$) satisfies the following mathematic inequality associated with a threshold value (E):

$$-E \leq T_1 \leq E$$

In some examples, the processing circuitry may set the threshold value (E) based on the combustible gaseous substance that the gas sensing apparatus is configured to measure. For example, the processing circuitry may set the threshold value (E) as one-percent (1%) of the lower explosive limit of the combustible gaseous substance. In some examples, the processing circuitry may set the threshold value (E) based on other parameters (for example, a safety threshold parameter of a safety system).

If, at block 809, the processing circuitry determines that the first reading ($T_1$) satisfies the threshold (for example, when the first reading ($T_1$) is not more than threshold value (E) and not less than negative of the threshold value (−E)), the processing circuitry may proceed to block 819 and the method 800 ends. In other words, the processing circuitry may determine that the first reading ($T_1$) can be used to calculate the concentration level of the combustible gaseous substance, and that there is little to no baseline drift of the sensing circuitry.

If, at block 809, the processing circuitry determines that the first reading ($T_1$) does not satisfy the threshold (for example, when the first reading ($T_1$) is more than threshold value (E) or less than the negative of the threshold value (−E)), the processing circuitry may proceed to block 811. In other words, the processing circuitry may determine that there is baseline drift in the sensing circuitry, and that the first reading ($T_1$) may contain inaccuracies due to the baseline drift.

While block 809 illustrates an example embodiment of using a threshold to determine whether to calculate a compensated reading of the gas sensing apparatus, it is noted that other embodiments may determine whether to calculate a compensated reading based on other parameters. For example, the processing circuitry may determine that the gas sensing apparatus has been in contact with the combustible gaseous substance for a pre-determine amount of time (for example, 3 hours), and may trigger the operation as illustrated in block 811.

At block 811, the processing circuitry may cause the supply of a stimulate voltage $S_2$ to a sensing circuitry of an example gas sensing apparatus (such as the sensing circuitry described above in connection with FIG. 6).

As described above, the stimulate voltage ($S_2$) is lower than the working voltage ($S_1$), and may not cause any combustible gaseous substance to react on the detector element. For example, the stimulate voltage ($S_2$) may be low enough to avoid overheating the detector element (for example, the temperature being lower than 200° C.), and thus may cause the gaseous substance to remain inert on the detector element.

In some examples, the stimulate voltage ($S_2$) may be a constant voltage between 0.1 V (inclusive) and 0.2 V (inclusive). In some examples:

$$S_2=0.2 \text{ V}$$

In some examples, the stimulate voltage ($S_2$) of block 811 of FIG. 8 may be the same as the stimulate voltage ($S_2$) of block 712 of FIG. 7.

After the stimulate voltage ($S_2$) is supplied to the sensing circuitry, the processing circuitry may determine and record a second output ($Z_{2,r}$) based on a constant, non-transitory signal received from the sensing circuitry at block 813.

In some examples, the second output ($Z_{2,r}$) may correspond to the voltage difference of a sensing circuitry in response to the stimulate voltage ($S_2$). For example, referring back to FIG. 6, the processing circuitry may record a second output ($Z_{2,r}$) that corresponds to the voltage difference ($S_{AB}$) of the sensing circuitry. The sensing circuitry may comprise a Wheatstone bridge circuit, and the processing circuitry may determine and record the second output ($Z_{2,r}$) that corresponds to the voltage difference ($S_{AB}$) in the Wheatstone bridge circuit of the sensing circuitry.

In some examples, when the stimulate voltage ($S_2$) is supplied to the sensing circuitry, the sensing circuitry may be in contact with the same combustible gaseous substance that the gas sensing apparatus is detecting in connection with block 805 described above. In comparison with the first output ($O_r$) of block 805, the second output ($Z_{2,r}$) may only correspond to voltage difference that is caused by baseline shift of the gas sensing apparatus, as there is no reaction of the combustible gaseous substance on the detector element due to the low voltage of the stimulate voltage ($S_2$).

In some examples, the processing circuitry may store the second output ($Z_{2,r}$) in a memory circuitry that is in electronic communication with the processing circuitry.

At block 815, the processing circuitry may calculate a value ($Z_{1,0}'$) that may, for example, account for the possible baseline drift of the gas sensing apparatus when a simulate voltage is supplied. In particular, the processing circuitry may calculate the value $Z_{1,0}'$ based at least in part on the second output ($Z_{2,r}$). For example, the value ($Z_{1,0}'$) may be calculated based on the following equation:

$$Z_{1,0}'=K \times S_1+Z_{2,r}-Z_{1,0}+b_0$$

where K is the coefficient and $b_0$ is the intercept (as described above in connection with blocks 716 and 718 of FIG. 7), $S_1$ is the working voltage, $Z_{1,0}$ is the output under the zero condition when simulate voltage is supplied (for example, as described in block 706 of FIG. 7), $Z_{2,r}$ is the output when stimulate voltage is supplied.

At block 817, the processing circuitry may calculate a compensated reading ($T_1'$) based at least in part on the first output value ($O_1$) and the value ($Z_{1,10}'$) (which is calculated based in part on the second output ($Z_{2,r}$)). For example, the compensated reading ($T_1'$) may be calculated based on the following equation:

$$T_1' = \frac{O_1 - Z_{1,0}'}{SEN_1}$$

where $O_1$ is the output from the sensing circuitry when simulate voltage is supplied, and $SEN_1$ is the sensitivity of the sensing circuitry (for example, as described in block 710).

Comparing the calculation of the first reading ($T_1$) at block 807 and the calculation of the compensated reading ($T_1'$), it is noted that the calculation of compensated reading ($T_1'$) utilizes the value ($Z_{1,0}'$) that may account for any possible baseline drift of the gas sensing apparatus. As such, the compensated reading ($T_1'$) may indicate a concentration level of the gaseous substance with an improved accuracy than the first reading ($T_1$).

In some examples, the compensated reading ($T_1'$) may be implemented in a variety of environments, scenarios, and industries to, for example, improve work safety and/or prevent injuries. For example, an example gas sensing apparatus in accordance with various embodiments of the present disclosure may be suitable as part of a security system in an oil drilling environment to, for example, detect whether combustible gaseous substance is at or close to a hazardous level. In some examples, the gas sensing apparatus may transmit the compensated reading ($T_1'$) to a processing circuitry that may be within the gas sensing apparatus, or to a processing circuitry outside the gas sensing apparatus via wireless external communication networks using any of a variety of protocols (such as, for example, Bluetooth®, ZigBee). The processing circuitry may determine whether the concentration level as indicated by the compensated reading ($T_1'$) satisfies a hazardous threshold. If so, the processing circuitry may trigger a warning (such as an audio alarm through a speaker element that is connected to the processing circuitry) to caution the user that the combustible gaseous substance has reached a hazardous level.

The method 800 ends at block 819.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. A method for calculating a compensated reading of a gas sensing apparatus, the method comprising:
   causing a first supply of a working voltage to a sensing circuitry of the gas sensing apparatus, wherein the sensing circuitry comprises a first circuit branch and a second circuit branch electronically coupled in parallel;
   determining a first output of the sensing circuitry, wherein the first output corresponds to a first voltage difference between the first circuit branch and the second circuit branch in response to the working voltage;
   generating a first reading of the gas sensing apparatus based at least in part on the first output;
   causing a second supply of a stimulate voltage to the sensing circuitry, wherein the stimulate voltage is lower than the working voltage to ensure a gaseous substance in contact with the gas sensing apparatus remains inert at the stimulate voltage, wherein a detector element and a compensator element are electronically coupled on the first circuit branch, wherein the working voltage causes the gaseous substance to react on the detector element and the stimulate voltage causes the gaseous substance to remain inert on the detector element;
   determining a second output of the sensing circuitry, wherein the second output corresponds to a second voltage difference between the first circuit branch and the second circuit branch in response to the stimulate voltage; and
   calculating the compensated reading of the first reading of the gas sensing apparatus, wherein the first reading is compensated based at least in part on the first output and the second output, wherein the compensated reading corresponds to a concentration level of the gaseous substance in contact with the gas sensing apparatus.

2. The method of claim 1, wherein a first resistor and a second resistor are electronically coupled on the second circuit branch.

3. The method of claim 1, wherein the detector element comprises a first metal wire coil covered in a catalytic material, wherein the compensator element comprises a second metal wire coil covered in a non-catalytic material.

4. The method of claim 1, wherein, prior to causing the second supply of the stimulate voltage, the method further comprises:
   determining that the first reading does not satisfy a threshold.

5. The method of claim 1, wherein the working voltage is between 2 volts (inclusive) and 4.5 volts (inclusive), wherein the stimulate voltage is between 0.1 volts (inclusive) and 0.2 volts (inclusive).

6. The method of claim 5, wherein the working voltage is 3 volts, wherein the stimulate voltage is 0.2 volts.

\* \* \* \* \*